United States Patent
Gargus et al.

(10) Patent No.: US 10,802,029 B2
(45) Date of Patent: *Oct. 13, 2020

(54) DEFECTIVE CALCIUM SIGNALING AS A TOOL IN AUTISM SPECTRUM DISORDERS

(71) Applicant: The Regents of the University of California, Oakland, CA (US)

(72) Inventors: John Jay Gargus, Irvine, CA (US); Galina Schmunk, Irvine, CA (US); Ian Parker, Irvine, CA (US); Ian Smith, Irvine, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/224,043

(22) Filed: Dec. 18, 2018

(65) Prior Publication Data

US 2019/0128898 A1    May 2, 2019

Related U.S. Application Data

(63) Continuation-in-part of application No. 15/750,492, filed as application No. PCT/US2016/045881 on Aug. 5, 2016, which is a continuation-in-part of application No. 14/821,555, filed on Aug. 7, 2015, now abandoned.

(60) Provisional application No. 62/219,085, filed on Sep. 15, 2015, provisional application No. 62/035,412, filed on Aug. 9, 2014.

(51) Int. Cl.
| | |
|---|---|
| *C12Q 1/68* | (2018.01) |
| *G01N 33/567* | (2006.01) |
| *G01N 33/68* | (2006.01) |
| *C12N 15/113* | (2010.01) |
| *C12N 15/115* | (2010.01) |
| *C07K 16/00* | (2006.01) |
| *G01N 33/84* | (2006.01) |

(52) U.S. Cl.
CPC ......... *G01N 33/6872* (2013.01); *C07K 16/00* (2013.01); *C12N 15/113* (2013.01); *C12N 15/115* (2013.01); *G01N 33/84* (2013.01); *G01N 2333/705* (2013.01); *G01N 2458/30* (2013.01); *G01N 2800/28* (2013.01); *G01N 2800/30* (2013.01)

(58) Field of Classification Search
None
See application file for complete search history.

(56) References Cited

U.S. PATENT DOCUMENTS 7,604,948 B2   10/2009 Amaral et al.
2011/0256565 A1   10/2011 Schon et al.

FOREIGN PATENT DOCUMENTS

WO   WO2017027412 A1   2/2017

OTHER PUBLICATIONS

MacDonald, R., et al.; Assessing progress and outcome of early intensive behavioral intervention for toddlers with autism; Research in Developmental Disabilities 35.12: 3632-3644; 2014.
Jacobson, J., et al.; Cost-benefit estimates for early intensive behavioral intervention for young children with autism-general model and single state case; Behavioral Interventions 13: 201-226; 1998.
Anderson, D. et al.; Predicting young adult outcome among more and less cognitively able individuals with autism spectrum disorders; Journal of Child Psychology and Psychiatry 55.5: 485-494; 2014.
International Search Report issued in PCT Application No. PCT/US2016/045881, dated Dec. 16, 2016.
Khan et al. "Subtype-selective regulation of IP3 receptors by thimerosal via cysteine residues within the IP3-binding core and suppressor domain." Biochemical Journal 451.2 (2013): 177-184.
Schmunk et al. "Reduced IP3-Mediated Ca2+ Signaling in Autism Spectrum Disorders in theContext of Fragile X and Tuberous Sclerosis Syndromes.", (Biophysical Journal 108.2:105a; Jan. 27, 2015) [retrieved on Sep. 15, 2016 from http://www.cell.com/biophysj/pdf/S0006-3495(14)01809-8.pdf].
Smith et al "Imaging the quantal substructure of single IP3R channel activity during Ca2+ puffs in intact mammalian cells." Proceedings of the National Academy of Sciences 106.15 (2009): 6404-6409.
Nguyen et al. Intracellular calcium dysregulation in autism spectrum disorder: An analysis of converging organelle signaling pathways. Biochimica et Biophysica Acta (BBA)—Molecular Cell Research vol. 1865, Issue 11, Part B, Nov. 2018, pp. 1718-1732.
Lu et al. Support for calcium channel gene defects in autism spectrum disorders. Molecular Autism 2012, 3:18.
Ripke et al. Genome-wide Association Analysis Identifies 14 New Risk Loci for Schizophrenia. Nat Genet. Oct. 2013 ; 45(10): 1150-1159. doi:10.1038/ng.2742.
Sanders et al. Insights into Autism Spectrum Disorder Genomic Architecture and Biology from 71 Risk Loci. Neuron. Sep. 23, 2015; 87(6): 1215-1233. doi:10.1016/j.neuron.2015.09.016.
Schmunk et al. Shared functional defect in IP3R-mediated calcium signaling in diverse monogenic autism syndromes. Transl Psychiatry (2015) 5, e643; doi:10.1038/tp.2015.123.
Smith et al. Mitochondrial and Ion Channel Gene Alterations in Autism. Biochim Biophys Acta. Oct. 2012; 1817 (10): 1796-1802. doi:10.1016/j.bbabio.2012.04.004.
Zeida'N-Chulia' et al. Exploring the Multifactorial Nature of Autism Through Computational Systems Biology: Calcium and the Rho GTPase RAC1 Under the Spotlight. Neuromol Med (2013) 15:364-383 DOI 10.1007/s12017-013-8224-3.

(Continued)

*Primary Examiner* — Olga N Chernyshev
(74) *Attorney, Agent, or Firm* — Nguyen Tarbet

(57) ABSTRACT

The present invention features methods that allow for diagnosing a risk for a patient or subject developing an Autism Spectrum Disorder, for identifying potentially therapeutic anti-ASD agents, and methods for treatment monitoring as specified in the independent claims.

4 Claims, 14 Drawing Sheets

(56) References Cited

OTHER PUBLICATIONS

Gargus, J. J. Genetic Calcium Signaling Abnormalities in the Central Nervous System: Seizures, Migraine, and Autism. vol. 1151, Issue1, The Year in Human and Medical Genetics 2009.Jan. 2009, pp. 133-156.

Lloyd-Fox et al. Cortical responses before 6 months of life associate with later autism. European Journal of Neuroscience, vol. 47, pp. 736-749, 2018.

Loth et al. The EU-AIMS Longitudinal European Autism Project (LEAP): design and methodologies to identify and validate stratification biomarkers for autism spectrum disorders. Molecular Autism (2017) 8:24. DOI 10.1186/s13229-017-0146-8.

Siddiqui et al. Mitochondrial Dysfunction in Autism Spectrum Disorders. Autism Open Access. Dec. 2016; 6 (5): . doi:10.4172/2165-7890.1000190.

Chen et al., Multiple Ca2R Signaling Pathways Regulate Intracellular Ca2R Activity in Human Cardiac Fibroblasts. J Cell Physiol. Apr. 2010;223(1):68-75.

Schmunk et al., High-throughput screen detects calcium signaling dysfunction in typical sporadic autism spectrum disorder, Scientific Reports, Feb. 1, 2017, 1-9, 7:40740, DOI: 10.1038/srep40740.

Siddiqui et al., Non-invasive measurement of a metabolic marker of infant brain function. Scientific Reports, May 2, 2017, 7:1330, DOI:10.1038/s41598-017-01394-z.

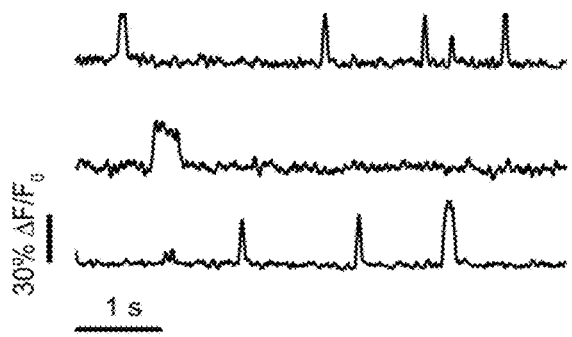
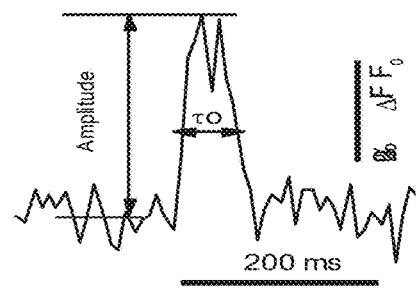
FIG. 8A                    FIG. 8B
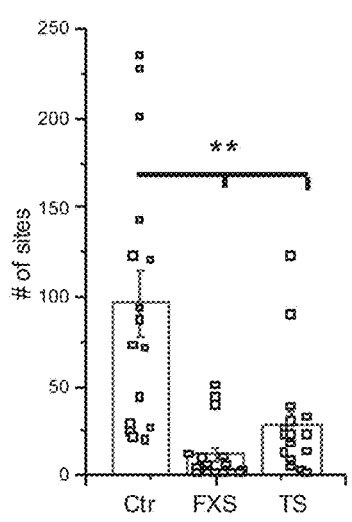
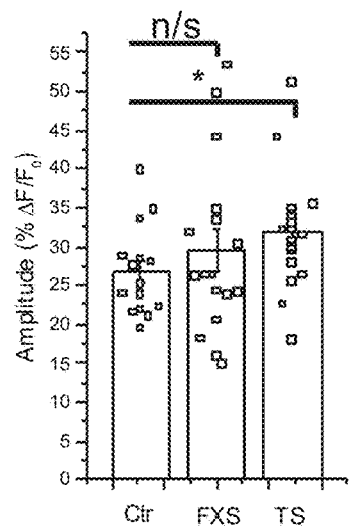
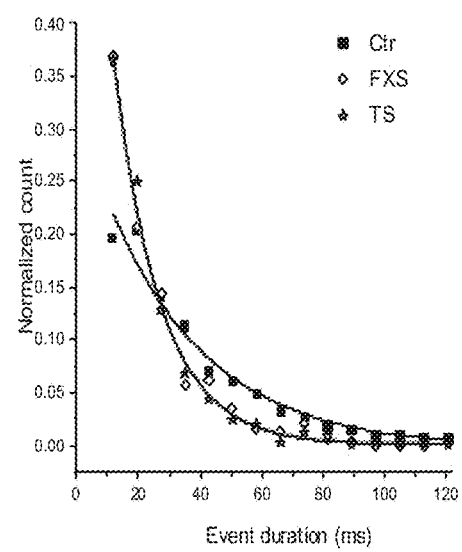
FIG. 8C           FIG. 8D           FIG. 8E

DEFECTIVE CALCIUM SIGNALING AS A TOOL IN AUTISM SPECTRUM DISORDERS

CROSS-REFERENCES TO RELATED APPLICATIONS

This application is a continuation-in-part and claims benefit of U.S. patent application Ser. No. 14/821,555, filed Aug. 7, 2015, which is a non-provisional and claims benefit of U.S. Provisional Application No. 62/035,412, filed Aug. 9, 2014, the specification(s) of which is/are incorporated herein in their entirety by reference.

This application is a continuation-in-part and claims benefit of U.S. patent application Ser. No. 15/750,492, filed Feb. 5, 2018, which is a 371 application of PCT/US16/45881, filed Aug. 5, 2016, which is a continuation-in-part and claims benefit of U.S. patent application Ser. No. 14/821,555, filed Aug. 7, 2015 and claims benefit of U.S. Provisional Application No. 62/219,085, filed Sep. 15, 2015, the specification(s) of which is/are incorporated herein in their entirety by reference.

BACKGROUND OF THE INVENTION

Autism spectrum disorder (ASD) is a neurological disorder characterized by signs and symptoms that include lack of social skills, language deficiency, and stereotypic repetitive behaviors. Each of the expressivity and severity of ASD symptoms is highly variable from patient to patient; and the etiology of ASD is ill defined. However, its high heritability suggests a strong genetic component; and it is generally understood that ASD can manifest from both monogenic and polygenic disorders.

Monogenic causes of ASD are responsible for only a few percent of all cases. Still, monogenic ASD models provide tractable systems for identifying and studying the molecular mechanisms and genetic architectures that underlie ASD. Fragile X syndrome (FXS) is the most common monogenic cause of ASD, and one of the most widely used and characterized ASD models. FXS is caused by a pathogenic expansion of a CGG-repeat on the X chromosome, leading to transcriptional silencing of the fragile X mental retardation (FMR1) gene. The fragile X mental retardation protein (FMRP) normally binds to several mRNAs, regulating their translation. The loss of FMRP in FXS patients leads to substantial cognitive impairment and intracellular signaling defects, both in humans and in mice. FMR1 knockout mouse lines are available and amount to tractable animal models for ASD.

Tuberous sclerosis (TS) is another monogenic cause of ASD. It is caused by dominant mutations in one of two genes, $TSC_1$ or $TSC_2$, which code for the proteins hamartin and tuberin, respectively. Hamartin and tuberin proteins form a functional signaling complex; and the disruption of these genes in the brain results in abnormal cellular differentiation, migration, and proliferation. $TSC_1$ and $TSC_2$ knockout mice are also available and amount to tractable animal models for ASD.

As autism is a complex, also polygenic disorder again characterized by difficulties in social interaction, verbal and nonverbal communication and repetitive behaviors. Previous work has indicated that ASD can be syndromic, caused by a strong single gene mutation, or sporadic, caused by a combination of genetic and environmental factors. Currently, ASD is projected to affect up to 2% of children who are diagnosed using behavioral assessments. While behavioral therapy instituted at the earliest possible time has proven beneficial, no drugs targeting ASD's core deficiencies are available.

The socioeconomic burden of ASD is enormous, currently estimated at over $268 billion per year in the USA alone. The rising rate of ASD, and the lack of drugs targeting its core symptoms, cry out for research into the development of new therapies. Drug development has proven to be problematic because of the limited understanding of the pathophysiology of ASD, the heterogeneity of symptoms, and difficulties in modeling the disease in vitro and in vivo. This is exemplified by the clinical failure of two large trials targeting the mGluR5 receptor.

Early identification is paramount for effective treatment, yet the average age of diagnosis is about 4 years. A long-standing goal is to identify a biomarker to aid early diagnosis. Although genome sequencing has identified>800 loci contributing susceptibility to ASD these amount to too many targets, each with too small an effect to be useful. However, many loci cluster in common signaling pathways, leading to the convergence hypothesis that genes conferring susceptibility to ASD converge at a signaling 'hub', resulting in disrupted downstream signaling that might reliably track ASD susceptibility. The present invention is based on a specific defect in intracellular Ca2+ signaling through the inositol trisphosphate receptor (IP3R), which appears ubiquitous among five forms of monogenic ASD and in multiple patients with sporadic ASD (i.e. without known cause), that is functionally-similar to channelopathy disease-causing ion channel mutations, but that in these cases of ASD is not associated with a mutation in the IP3R channel itself.

The IP3R mediates crucial neuronal functions affected in ASD including a newly recognized infant biomarker of defective mitochondrial bioenergetics, neuronal excitability and neurotransmitter release, highlighting its integral position. Without wishing to limit the invention to a particular theory or mechanism, IP3R serves as a signaling hub where different genes converge to exert their deleterious effect in ASD. Growing evidence supports a role of Ca2+ signaling in the pathogenesis of ASD. Inositol trisphosphate (IP3)-mediated Ca2+ release from intracellular stores participates in a variety of functions, from synaptic plasticity and memory, to long-term gene transcription changes and immune response. IP3 is produced upon stimulation of G-protein coupled receptors (GPCR) and binds to IP3R/channel in the membrane of the endoplasmic reticulum (ER), liberating Ca2+ sequestered in the ER lumen into the cytoplasm.

FIELD OF THE INVENTION

The present invention relates to methods of diagnosing a risk for a patient or subject developing an autism spectrum disorder (ASD). Certain embodiments relate to methods of identifying potentially therapeutic anti-ASD agents and methods for treatment monitoring.

DESCRIPTION OF RELATED ART INCLUDING INFORMATION DISCLOSED

Recent advances using monogenic animal models to understand the syndromic forms of ASD such as fragile X (FXS), Rett syndrome, and tuberous sclerosis (TSC) have provided insights into the pathophysiology of these conditions. However, identified monogenic causes of ASD are responsible for only a few percent of all cases, with the majority caused by a complex interplay of various genetic and environmental factors.

Genome-wide association studies (GWAS) have identified many "risk" alleles for ASD, which cluster in common signaling pathways. This has led to a convergence hypothesis, proposing that key hubs within signaling pathways may be a point of convergence for many of the mutated genes to exert their deleterious effects. Recently, a GWAS of single nucleotide polymorphisms (SNPs) in over 30,000 cases revealed alterations in several Ca2+ channel genes associated with neurological disorders, including ASD, and other studies strongly implicated defects in Ca2+ channels and Ca2+-associated proteins with susceptibility to ASD.

The potential involvement of disrupted Ca2+ signaling in ASD was not previously mechanistically understood. The present invention builds on the unique finding that IP3-induced Ca2+ signaling is deficient in three distinct monogenic models of ASD. Although not bound by any particular theory, IP3R mediated Ca2+ signaling appears to play a "hub" role in ASD pathogenesis.

Ca2+ is a ubiquitous second messenger involved in a variety of cellular functions, including excitability, motility, cell secretion, gene expression, and apoptosis. Ca2+ signaling is highly localized, ensuring high specificity of cellular responses dependent on the source of Ca2+. IP3 is a ubiquitous and highly conserved second messenger that performs a variety of cellular functions, such as signal transduction and cell proliferation, in a wide range of cell types. IP3 mediates Ca2+ release from intracellular stores in neurons, a function that has been implicated in synaptic plasticity and memory, neuronal excitability, neurotransmitter release, and long-term changes in gene transcription.

The IP3R forms a Ca2+-permeable channel in the ER membrane, and its opening allows the release of ER sequestered Ca2+ into the cytosol. IP3R channel opening requires binding of IP3 and Ca2+ to cytosolic sites of the IP3R channel. IP3R channel gating by Ca2+ is biphasic, such that small increases of cytosolic Ca2+ induce channel opening, whereas larger increases of cytosolic Ca2+ cause inactivation. The positive feedback aspect of IP3R channel gating underlies the process known as Ca2+-induced Ca2+ release (CICR), in which Ca2+ is released in a regenerative manner that may either: (i) remain restricted to a cluster of IP3Rs, producing local Ca2+ signals known as Ca2+ puffs, or (ii) propagate throughout the cell as a saltatory wave, propagated by the recruitment of multiple puff sites and successive cycles of Ca2+ puffs, diffusion, and CICR. Thus, IP3-mediated Ca2+ signaling comprises a hierarchy of Ca2+ signaling events of differing magnitudes, and the spatial patterning and distribution of IP3Rs is critical to proper Ca2+ signaling (FIG. 2).

An energy-deficient endophenotype of ASD may result from disrupted IP3R/Ca2+ signaling. Without wishing to limit the invention to any theory or mechanism, the invention features a novel link involving mitochondrial energetics. Biomarkers of mitochondrial energy deficiency have been associated with a subset of ASD and this finding was confirmed in ~5% of ASD cases among a Portuguese population. A similar pattern of mitochondrial energy-deficiency is reported in syndromic ASD associated with Rett syndrome (RS) and in mouse models of RS; and the protein products of TSC1 and TSC2 regulate mTOR, a key regulator of mitochondrial function. A UK-based EU-AIMS collaborating consortium reported imaging of deficient neuronal mitochondrial cytochrome C oxidation/reduction response to "social brain" visual and auditory tasks observed in 4-6 month-old infants who would, at age 3 years, be diagnosed with ASD by standard ADOS testing. This invention of a cellular phenotype (e.g., IP3R-mediated Ca2+ signaling) is consistent and synergistic with this functional brain imaging phenotype, and might be used to mutually support one another to recognize abnormal early brain development that is associated with and predictive of the ultimate diagnosis of ASD. Without wishing to limit the invention to any theory or mechanism, deficiencies in mitochondrial function may be linked to IP3 signaling, suggesting a direct role of constitutive Ca2+ release through IP3Rs in sustaining normal mitochondrial energetics and a deficiency in IP3R function may be associated with ASD, potentially including compromised mitochondrial bioenergetics and autophagy.

Disrupted functioning of ER Ca2+ release channels is observed in cognitive disorders including Alzheimer's and Huntington's diseases, and IP3Rs have recently been identified among the genes affected by rare de novo copy number variations in ASD patients. Moreover, the ER participates in a host of cellular responses to environmental stressors. Given that proper functioning of the IP3R/Ca2+ signaling pathway is critical for normal neuronal development and function, without wishing to limit the present invention to a particular theory or mechanism, the disruption of the IP3R/Ca2+ signaling pathway plays a key 'hub' role in the pathogenesis of ASD and this pathway can serve as a diagnostic biomarker and potential target for novel drug discovery. As such, this form of Ca2+ signaling is a prospective ASD biomarker and therapeutic target.

Considering that there are no alternatives to subjective behavioral tests (the ADOS, Autistic Diagnostic Observation Scale)) to make a diagnosis, chromosomal and genetic tests have become popular. However, this statistical genetic approach requires an assessment of nearly 1000 ASD risk genes and that each has an impact that is so low (odds ratio of 1.02 vs control risk of 1.00) that one can't reasonably counsel ASD risk. These genetic techniques are costly, but unlike typical disease panels that may contain a dozen genes, ASD gene panels can produce an ambiguous diagnostic signal, which can create a liability risk in the absence of a reliable phenotypic outcome. Examples of DNA-based diagnostics include ARISK, ARISK2, FirstStep, CombiSNP, DevACT and DevSEEK. Most of these sequence-based services are being used to bolster confidence in the diagnosis of ASD after behavioral testing, rather than diagnose ASD on their own.

As there are no other known diagnostic functional biomarkers for ASD on the market, the present invention would be the first and will create its own market segment rather than competing with existing genetic sequence testing companies. ASD has a high prevalence in males and has a dramatically increased recurrence risk (~20% vs 1-2%) in families with history of ASD. Taking advantage of discarded circumcision foreskin, the present invention can be incorporated in a battery of newborn screening tests that could be routinely performed in U.S. hospitals along with current dry blood spot newborn screening.

BRIEF SUMMARY OF THE INVENTION

The present invention features methods that allow for diagnosing a risk for a patient developing an ASD, for identifying potentially therapeutic anti-ASD agents, and methods for treatment monitoring as specified in the independent claims. Embodiments of the invention are given in the dependent claims. Embodiments of the present invention can be freely combined with each other if they are not mutually exclusive.

The present invention features a method for diagnosing a risk for developing ASD in a subject. The method comprises: a. obtaining a biological sample containing cells from the subject being evaluated for ASD; b. using a reference tissue type-matched cell from a control healthy neurotypically developing individual without known ASD risk factors and without ASD and/or using a positive reference tissue type-matched cell from ASD diagnosed individuals; c. independently culturing the cells from (a) and (b); d. measuring the level of $IP_3R$ $Ca^{2+}$ signaling activity in both sets of the cultured cells from (c) in response to an agonist of $IP_3R$ $Ca^{2+}$ signaling using a $Ca^{2+}$ fluorescent probe and measuring the amount of fluorescence emitted by the probe; e. comparing the: a) peak signal height; b) area under the signal curve; and c) signal rate of rise of $IP_3R$ $Ca^{2+}$ signaling activity obtained from (d); and f. identifying "zones of susceptibility" to determine a susceptibility to developing ASD based on the levels of $IP_3R$ $Ca^{2+}$ signaling activity in (e), wherein the zones of susceptibility comprise: 1) signal "dead" zone, wherein the subjects have undetectable calcium signaling, seen only in subjects diagnosed with ASD, and therefore the test subjects are designated as a first group of subjects who are susceptible to developing ASD; 2) "neurotypical" zone, wherein subjects have at least 40% of control cell $IP_3R$ $Ca^{2+}$ signaling activity, a level rarely seen in ASD subjects, and therefore the subjects are designated as a second group of subjects who are less susceptible than the first group to developing ASD, and 3) indeterminant zone between 0-40% control signal, wherein the subjects are designated as a third group of subjects who have indiscriminate susceptibility to developing ASD and requiring further evaluation for susceptibility of developing ASD.

The present invention further features a method for determining a susceptibility to developing ASD prenatally in a subject, the method comprising: a. obtaining an amniocentesis from a pregnant subject containing fibroblastic amniocytes from the fetus; b. using a reference tissue type-matched cell from control individuals without known ASD risk factors; c. using a positive reference tissue type-matched cell from ASD diagnosed individuals; d. independently culturing the cells from (a) and (b) and (c); e. measuring the level of $IP_3R$ $Ca^{2+}$ signaling activity in all sets of the cultured cells from (d) in response to an agonist of $IP_3R$ $Ca^{2+}$ signaling using a $Ca^{2+}$ fluorescent probe and measuring the amount of fluorescence emitted by the probe; f. comparing the: a) peak signal height; b) area under the signal curve; and c) signal rate of rise of $IP_3R$ $Ca^{2+}$ signaling activity obtained from (e); and g. identifying "zones of susceptibility" to determine a susceptibility to developing ASD based on the levels of $IP_3R$ $Ca^{2+}$ signaling activity in (e), wherein the zones of susceptibility comprise: 1) signal "dead" zone, wherein the subjects have undetectable calcium signaling, seen only in subjects with diagnosed with ASD, and therefore the test subjects are designated as a first group of subjects who are susceptible to developing ASD; 2) "neurotypical" zone, wherein subjects have at least 40% of control cell $IP_3R$ $Ca^{2+}$ signaling activity, a level rarely seen in ASD subjects, and therefore the subjects are designated as a second group of subjects who are less susceptible than the first group to developing ASD, and 3) indeterminant zone between 0-40% control signal, wherein the subjects are designated as a third group of subjects who have indiscriminate susceptibility to developing ASD and requiring further evaluation for susceptibility of developing ASD.

The present invention also features a method for screening a test agent to treat a subject with ASD. The method comprises the following steps: a. using a reference tissue type-matched cell from control neurotypical individuals without known ASD risk factors; b. using a positive reference tissue type-matched cell from subjects diagnosed with ASD; c. independently culturing the cells from (a) and (b); d. leaving one sample of the (a) population unexposed, exposing one sample of the (a) population and one of the (b) population of isolated cells to a range of doses of the test agent beginning at 0 test agent; e. contacting each of the cultured cells from (d) with an agonist of $IP_3R$ $Ca^{2+}$ signaling and fluorescent $Ca^{2+}$ indicator; f. measuring fluorescence emitted by the fluorescent $Ca^{2+}$ indicator in the ASD (b) population of isolated cells with different doses of test agent to determine a test agent dose dependent $IP_3R$ $Ca^{2+}$ signaling activity; g. measuring an amount of fluorescence emitted by the $Ca^{2+}$ fluorescent probe in the (a) population of isolated cells unexposed to the test agent to determine the neurotypical control $IP_3R$ $Ca^{2+}$ signaling activity; and h. detecting a dose-dependent difference (e.g., increase) of $IP_3R$ $Ca^{2+}$ signaling activity in the test agent-exposed ASD (b) population of cells. For control signaling, the same comparison is made with the neurotypical (a) control population for $IP_3R$ $Ca^{2+}$ signaling activities in (g), over the range of doses of the test compound. The method would indicate that the test agent is a potentially therapeutic anti-ASD agent when the $IP_3R$ $Ca^{2+}$ signaling activity in the ASD (b) population of isolated cells increases to potentially become comparable to that of the (a) population of isolated untreated control cells. An ideal agent would not have a significant effect on the (a) neurotypical cells.

The present invention further features a method of using functional biomarkers to develop treatment strategies for subjects with ASD, the method comprising: a. obtaining a biological sample containing fibroblast cells from the subject with ASD; b. assaying the biological sample to determine the presence (at or above detectable limit or threshold) or absence (below limit of detection or threshold) of one or more ASD biomarkers comprising one or more of 1) a reduced $IP_3R$ $Ca^{2+}$ signaling activity level as in 1, 2) a mitochondrial energy-deficiency profile, and/or 3) genomic signature; c. assessing the subject to determine the presence or absence of one or more ASD biomarkers comprising one or more of absence or low electroencephalography (EEG) connectivity signal and/or low infrared laser spectroscopy cortical neuron mitochondrial (IRLS) signal, d. diagnosing a risk for ASD based on the presence of one or more ASD biomarkers from (b) and/or (c).

The present invention also features a method of treating ASD in a subject, comprising: providing behavioral therapy and/or providing a composition comprising one or more activators of dysfunctional IP3-mediated Ca2+ signaling, and administering a therapeutically effective dosage of the composition in (b) to the subject.

The present invention further features a method of monitoring treatment for a subject with ASD, the method comprising: a. obtaining a biological sample containing cells from the subject being evaluated for ASD; b. using a reference tissue type-matched cell from a control healthy neurotypically developing individual without known ASD risk factors and without ASD and/or using a positive reference tissue type-matched cell from ASD diagnosed individuals; c. independently culturing the cells from (a) and (b); d. measuring the level of $IP_3R$ $Ca^{2+}$ signaling activity in both sets of the cultured cells from (c) in response to an agonist of $IP_3R$ $Ca^{2+}$ signaling using a $Ca^{2+}$ fluorescent probe and measuring the amount of fluorescence emitted by the probe; e. comparing the: a) peak signal height; b) area under the signal curve; and c) signal rate of rise of IP$_3$R Ca$^{2+}$ signaling activity obtained from (d); and f. identifying "zones of susceptibility" to determine a susceptibility to developing ASD based on the levels of IP$_3$R Ca$^{2+}$ signaling activity in (e), wherein treatment response monitoring is based on the zones of susceptibility that comprise: 1) signal "dead" zone, wherein the subjects have undetectable calcium signaling, seen only in subjects with diagnosed with ASD, and therefore suggesting no or little treatment response or little improvement/benefit to therapy; 2) "neurotypical" zone, wherein subjects have at least 40% of control cell IP$_3$R Ca$^{2+}$ signaling activity, a level rarely seen in ASD subjects, and therefore suggesting substantial improvement in response to therapy (or treatment response) and 3) indeterminant zone between 0-40% control signal, wherein subjects have indiscriminate response that may reflect a level of improvement from the baseline prior scores. A therapeutic response would be recognized as an improvement in the signal above the subject's signaling prior to therapy.

One of the unique and inventive technical features of the present invention is the use of skin fibroblasts and specific agonist-induced IP$_3$R Ca$^{2+}$ signaling activity. Without wishing to limit the invention to any theory or mechanism, it is believed that the technical feature of the present invention advantageously provides for ease of biological sample collection (e.g., from skin) and early quantitative objective diagnosis (e.g. using foreskins of newborns) and a distinct component of Ca$^{2+}$ signaling activity measured through specific agonist-induced IP$_3$R Ca$^{2+}$ signaling. None of the presently known prior references or work has the unique inventive technical feature of the present invention.

Furthermore, the prior references teach away from the present invention. For example, ASD is considered to be a "brain" disease, and one that impacts only specific cortical circuits and only at the late age at which onset of symptoms arise at age 2. With conventional theory, it would make no sense to assay a skin cell, to assay signaling from an organelle ubiquitously found throughout the body cells or to be able to study a sample from newborn baby. Furthermore, the inventive state-of-the-art techniques of TIRFM and super-resolution microscopy and optical patch clamp technical analysis features of the present invention contributed to a surprising result. For example, that such a very large percentage of cases with this very heterogeneous disease show such a similar signaling defect.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWINGS

FIG. 2 illustrates different types of Ca$^{2+}$ signals produced by one or more IP$_3$R(s) in response to low, intermediate, and high IP$_3$ concentrations, which are, respectively, single-channel events, "blips"; elementary events, "puffs"; and global events, "waves". FIG. 2, right traces, are fluorescence traces of blip, puff, and wave Ca$^{2+}$ signaling events mediated by IP$_3$R(s).

FIG. 3A top, shows plots of mean peak Ca$^{2+}$ release exhibited by control and FXS human skin fibroblast cells loaded with calcium indicator Fluo-8 AM in response to ATP, the agonist that tests for the ASD phenotype.

FIGS. 8A-8E show IP3-mediated Ca2+ signaling in FXS and TSC fibroblasts is impaired at the level of local events. Data are from 17 FXS cells, 17 TSC cells, and 16 control cells (Ctr) matched to both experimental groups. FIG. 8A shows representative traces of individual events to illustrate their kinetics. FIG. 8B shows a single Ca2+ event shown on an expanded scale to illustrate measurements of peak amplitude and event duration at half-maximal amplitude. FIG. 8C shows the mean total numbers of Ca2+ release sites detected within cells during 40 s imaging records following uniform photo-release of i-IP3 within a cell.

FIG. 8D shows the mean amplitude of all events following the photolysis within a cell. FIG. 8e shows the distributions of event durations (at half maximal amplitude) derived from all events identified in FXS (open diamonds), TSC (stars) and control cells (black squares) (□o*). The data are fit by single-exponential distributions with time constants ($t_0$) of 15 ms (both FXS and TSC) and 32 ms (control). *=p-value<0.05; **=p<0.01, n/s—non-significant.

FIG. 9A shows locations of spontaneous Ca2+ signals in WT fibroblasts. FIG. 9B shows Ca2+ events from selected sites in FIG. 9A. FIG. 9C shows numbers of sites in WT and FXS cells. FIG. 9D shows GFP-LC3 expression in WT cells showing ring-shaped structure characteristic of autophagosomes FIG. 9E shows background-subtracted fluorescence of GFP-LC3 for WT, FXS, TSC2 and sporadic ASD fibroblasts. N=10 for all experiments.

FIGS. 13A-13B show superimposed traces of single-cell $Ca^{2+}$ response to uncaging of ci-iP$_3$ in control (FIG. 13A) and FXS (FIG. 13B) progenitors. Arrow indicates time of the UV flash. FIG. 13C shows mean amplitudes and latencies to peak of $Ca^{2+}$ fluorescence signals in FXS progenitors (red) and matched controls (black).

FIG. 14A shows TIRF imaging of the local $Ca^{2+}$ microdomain around an open $IP_3R$ located in close proximity to the plasma membrane. FIG. 14B shows a comparison of puffs recorded by conventional wide-field fluorescence (grey) and by TIRF imaging with EGTA loaded (black). FIG. 14C shows an example of sites that show exclusively single-channel activity. FIG. 14D shows fluorescence trace showing multiple puffs evoked at a single site following photo-release of $IP_3$. FIG. 14E inset shows an individual puff recorded using the optical patch clamp on an expanded time scale illustrating step-wise changes in fluorescence arising from closings and openings of individual $IP_3R$ channels. Histogram shows the distribution of step levels as multiples of the single-$IP_3R$ channel (blip) fluorescence.

DETAILED DESCRIPTION OF THE INVENTION

Figure 1:
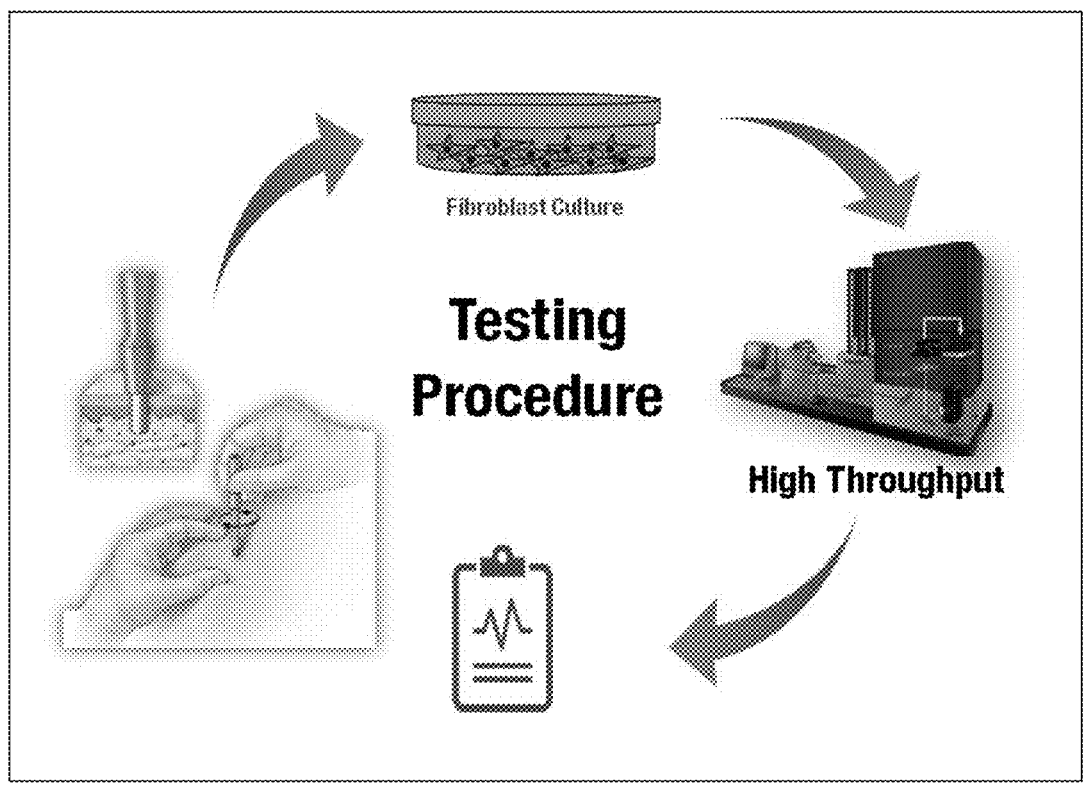
FIG. 1 shows a schematic overview of the present invention.

Referring now to FIGS. 1-14, the present invention features methods for diagnosing a risk for a patient developing an ASD and for identifying potentially therapeutic anti-ASD agents and methods for treatment monitoring. As summarized in FIG. 1, the present invention for diagnosing susceptibility to ASD in a subject comprises: obtaining a skin sample from the subject to be diagnosed; assaying the sample utilizing high throughput screening to determine $IP_3R$ $Ca^{2+}$ signaling activity levels (e.g., using FLIPR); and comparing signal activity level to a reference value from a healthy control subject; wherein a low activity level beneath the threshold for the reference control samples is indicative of susceptibility to ASD.

Embodiments of the invention provide methods of diagnosing a risk for a patient developing ASD. Such methods involve a step of identifying a reduced IP3R Ca2+ signaling activity level in cells from the patient comparable to matched cells from a known ASD (positive control) and substantially reduced compared to a known neurotypical (negative control) individual; and diagnosing a risk of the patient developing ASD when the IP3R activity level is reduced comparable to that of the known ASD positive control individual. Typically, in such methods, the patient and positive and negative control individuals are both human beings; and the cells from the patient and the cells from the control individuals are matched in tissue type.

In some embodiments, the patient and the positive and negative control individuals are of similar sex, gender, ethnicity, and age.

In some embodiments, the matched human tissue type consists essentially of skin fibroblast cells, peripheral blood cells, keratinocytes, umbilical cord or amniocentesis-derived cells. The biological samples comprise skin, foreskins, amniotic fluid, blood, umbilical cord and/or, cheek-swabbed epithelial cells. The cell type comprises a fibroblast obtained from skin, a fibroblast obtained from foreskin, a fibroblast obtained from umbilical cord or amniocentesis, an iPSC (induced-pluripotent stem cell)-derived cell, a blood cell, and/or an epithelial cell from a cheek-swab.

In some embodiments, the identification of the reduced IP3R Ca2+ signaling activity level in the patient further involves obtaining equivalent amounts of separately cultured and matching cells from the patient and from the control individual that have been loaded with a Ca2+ fluorescent indicator and contacted with an agonist of IP3R Ca2+ signaling. Then measuring, in the so loaded and contacted cells, an amount of fluorescence emitted by the fluorescent Ca2+ indicator; and comparing the measured amounts of emitted fluorescence.

In some embodiments, the fluorescent indicator of IP3R mediated Ca2+ signaling is a Fluo-8 AM, Fluo-3, Fluo-4, Rhod-2 and related derivatives; Cal 520 and its analogues; Calcium Green, Calcium Orange and related derivatives; Oregon Green BAPTA and related derivatives; Fura Red, GCaMPs or other genetically encoded calcium indicators.

In some embodiments, the agonist of IP3R Ca2+ signaling is at least one of an adenosine triphosphate and a caged inositol triphosphate or its analogues. Other agonists include, but are not limited to: Adenophostin A; nucleotides; glutamate or other GPCR agonists.

Certain embodiments of the present invention provide a method of identifying potentially therapeutic anti-ASD agents. Such methods include using two populations of cells comprising 1) a reference tissue type-matched cell from control neurotypical individuals without known ASD risk factors and 2) a positive reference tissue type-matched cell from subjects diagnosed with ASD. The steps of the method comprise: 1) independently culturing these two populations of isolated cells; 2) leaving one sample of the neurotypical population unexposed and exposing one sample of the neurotypical population and one of the ASD population of isolated cells to a range of doses of the test agent; 3) contacting each of the cultured cells from (2) with an agonist of $IP_3R$ $Ca^{2+}$ signaling and fluorescent $Ca^{2+}$ indicator; 4) measuring fluorescence emitted by the fluorescent Ca2+ indicator in the ASD population of isolated cells with different doses of the test agent to determine a test agent dose dependent IP3R Ca2+ signaling activity; 5) measuring an amount of fluorescence emitted by the $Ca^{2+}$ fluorescent probe in the neurotypical population of isolated cells unexposed to the test agent to determine the neurotypical control $IP_3R$ $Ca^{2+}$ signaling activity; and 6) detecting a difference (e.g., increase) in $IP_3R$ $Ca^{2+}$ signaling activity in the test agent-exposed ASD population of cells across the range of doses of the test agent. For the control IP3R Ca2+ signaling activities, the same comparison is made with the neurotypical (a) control population for $IP_3R$ $Ca^{2+}$ signaling activities over the range of doses of the test agent. In such methods, an increased IP3R Ca2+ signaling activity in the test agent-exposed ASD population of isolated cells to potential levels observed in the untreated (e.g., not exposed to the test agent) control population of isolated cells identifies the test agent as a potentially therapeutic anti-ASD agent. An ideal agent would not have a significant effect on the (a) neurotypical cells. Also, in such methods, each of the first and the second populations of cells: were isolated from the same type of tissue of an ASD patient; exhibit a reduced level of IP3R Ca2+ signaling activity as compared to matched cells isolated from an individual that does not have ASD; and comprise substantially the same number of cells.

In some embodiments, anti-ASD therapeutic agents of the invention are chemical compounds, antibodies, antibody fragments, siRNA molecules, antisense RNA molecules, aptomers, or the like.

In some embodiments, the IP3R Ca2+ signaling is neuronal.

EXAMPLES

The following are non-limiting examples of the present invention. It is to be understood that said examples are not intended to limit the present invention in any way. Equivalents or substitutes are within the scope of the present invention.

Cell System Models for ASD

This invention utilizes fibroblasts, which are readily obtained from skin biopsies and are already in routine clinical use for the diagnosis and development of therapeutic strategies of mitochondrial, peroxisomal and lysosomal organellar-based neurological diseases. The physiology of IP3 signaling in fibroblasts is well studied, providing a validated and convenient model that complements advanced imaging technologies to resolve IP3R functioning in intact cells at the single-molecule level. Although fibroblasts and neurons express differing proportions of the three subtypes of the IP3R, it has been recently demonstrated that the single-channel gating and conductance properties of the three types of IP3R are essentially the same. Finally, fibroblasts are readily obtainable from both disease and matched control subject populations. Thus, the present invention utilizes fibroblasts, which serve as a valid model to investigate the fundamental properties of neuronal IP3 signaling and an amenable model system for IP3/Ca2+ signaling as a biomarker and potential diagnostic tool for ASD. The present invention features a method to investigate the molecular mechanisms underlying this shared defect and its downstream signaling consequences.

Cell Culture

Human skin fibroblasts were purchased from Coriell Cell Repository. Cells were cultured in Dulbecco's Modified Eagle's Media (ATCC 30-2002) supplemented with 10% (v/v) fetal bovine serum and 1× antibiotic mix (penicillin/streptomycin) at 37° C. in a humidified incubator gassed with 95% air and 5% CO2, and used for up to 20 passages. Cells were harvested in Ca2+, Mg2+-free 0.25% trypsin-EGTA (Life Technologies) and sub-cultured on 96-well plates at a seeding density of $1.5 \times 10^4$ cells/well for 2 days before use.

High-Throughput Ca2+ Imaging

Skin fibroblasts were seeded in 96-well plates (e.g., clear-bottom black 96-well plates; Greiner Bio One catalogue # T-3026-16) at $3 \times 10^4$ cells per well and grown to confluency. On the day of the experiment, cells were loaded with membrane-permeant Ca2+ indicator Fluo-8 AM 4 µM in standard buffer solution (130 mM NaCl, 2 mM CaCl2), 5 mM KCl, 10 mM glucose, 0.45 mM KH2PO4, 0.4 mM Na2HPO4, 8 mM MgSO4, 4.2 mM NaHCO$_3$, 20 mM HEPES and 10 µM probenecid) with 0.1% fetal bovine serum for 1 h at 37° C., then rinsed with standard buffer solution. 100 µl of Ca2+-free solution was added to each well, and cells were allowed to equilibrate for 5 minutes prior to the experiment. The assay was then performed with a FLIPR instrument (Fluorescent Image Plate Reader, Molecular Devices, Sunnyvale, Calif.). Relative Fluorescent Units were measured during 120 s to determine kinetics reflecting the change in intracellular Ca2+ levels according to ATP addition. A basal read of plate fluorescence (470-495 nm excitation and 515-575 nm emission) was read for 2 seconds on the FLIPR. Next, 100 µl of 2×ATP (1 µM, 10 µM, 100 µM final concentration) in Ca2+-free Hank's Balanced Salt Solution (HBSS), or HBSS alone, were added to the appropriate wells. A real-time fluorescence measurement was immediately performed for 180 seconds of the assay, followed by addition of 100 μl of 3× ionomycin (to 10 μM final concentration), and the recording continued for another 30 sec. Fluorescence signals are expressed as a ratio ($\Delta F/F0$) of changes in fluorescence ($\Delta F$) relative to the mean resting fluorescence of the same well before stimulation (F0). Individual data were normalized to the maximum ionomycin response for each well obtained at the end of the experiment. Bars represent standard error mean. For experiments studying local Ca2+ signals, cells were loaded with Ca2+ indicator Ca1520, c-iIP3 and additionally incubated with 10 μM EGTA-AM for an hour. [Ca2+]i signals were imaged using an Apo TIRF 100× (NA=1.49) oil objective.

Single-Cell $Ca^{2+}$ Imaging

Cells seeded in glass-bottomed dishes were loaded with 4 μM Fluo-8 AM and 1 μM caged i-IP$_3$ (ci-IP$_3$) for 45 mins. [$Ca^{2+}$]; changes were imaged with a 40× oil objective at 30 frames sec$^{-1}$. A single flash of UV light was used to uncage i-IP$_3$. For local $Ca^{2+}$ signals, cells were loaded with $Ca^{2+}$ indicator Ca1520, c-iIP$_3$ and 10 μM EGTA-AM for an hour. [$Ca^{2+}$]; signals were imaged using an Apo TIRF 100× (NA=1.49) oil objective at 129 frames sec$^{-1}$.

Example 1 IP3-Mediated Ca2+ Signaling is Depressed in FXS and TSC Fibroblasts

To examine for defects in IP3-mediated signaling associated with ASD, a fluorometric imaging plate reader (FLIPR) was used to monitor cytosolic Ca2+ signals in skin fibroblasts from FXS, TS, and matched control subjects. Adenosine triphosphate (ATP) was applied to activate G-protein coupled receptors (GPCR)-linked purinergic P2Y receptors in Ca2+-free extracellular solution to exclude Ca2+ influx through plasmalemmal channels.

Skin fibroblast cell lines from each of five FXS patients and five ethnicity-, sex-, and age-matched unaffected donor-derived control fibroblast cell lines were obtained from the Coriell Cell Repository. Skin fibroblast cell lines from each of three TS, two TSC1 patients and one TSC2 patient, and three corresponding sex-, age- and ethnicity matched control fibroblast cell lines were also obtained from the Coriell Cell repository.

Figure 3A:
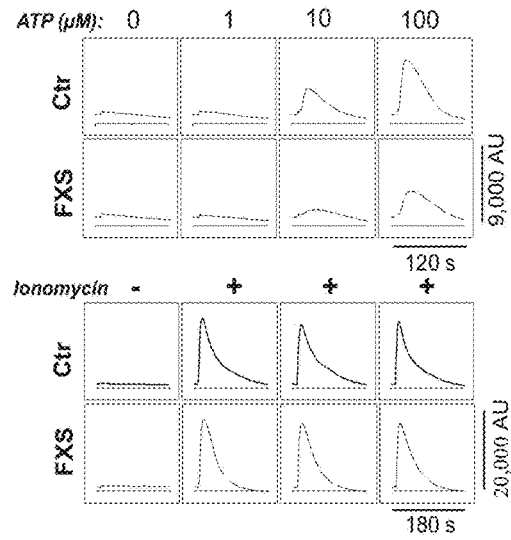
FIG. 3A bottom, shows plots of mean peak Ca$^{2+}$ release exhibited by control and FXS human skin fibroblast cells loaded with calcium indicator Fluo-8 AM in response to ionomycin, a potent and specific calcium ionophore. FXS and control cell lines demonstrate no difference between cells in maximal calcium signal (the calcium pool size).
Figure 3B:
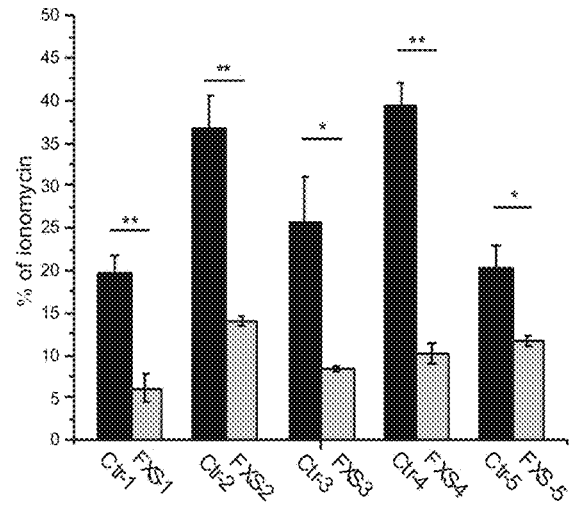
FIG. 3B shows plots of mean peak Ca$^{2+}$ release exhibited by 5 independent individual control and 5 independent individual FXS skin fibroblast cells induced with ATP normalized to corresponding maximal response to ionomycin. All FxS lines are significantly different (p<0.05) from controls.
Figure 3C:
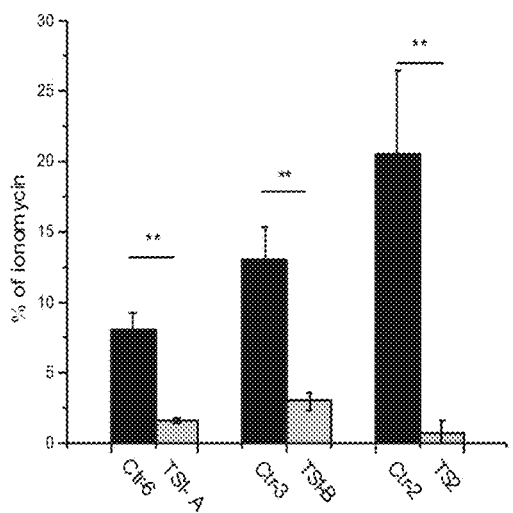
FIG. 3C shows a mean response of TSC1 and TSC2 and control cell lines to ATP as in FIG. 3B.
Figure 3D:
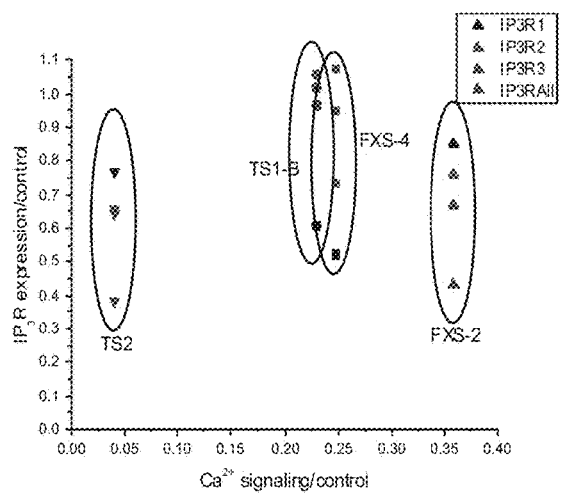
FIG. 3D shows a scatter plot showing IP$_3$R expression levels in TSC and FXS cell lines as % of matched controls vs. the mean ATP-evoked Ca$^{2+}$ signals in these cells relative to matched controls. Different symbols represent different cell lines. Here, and in other figures, error bars show ±1 SEM.

Responses were significantly depressed in FXS cells (FIG. 3A, top; FIG. 3B). This was not due to deficits in ER Ca2+ stores in FXS cells, as application of ionomycin in Ca2+-free media to completely liberate intracellular Ca2+ stores evoked similar signals in FXS and control cells (FIG. 3A, bottom). Cell lines from tuberous sclerosis (TSC1 and TSC2) patients further demonstrated deficits in ATP-evoked Ca2+ signals (FIG. 3C), again without any appreciable difference in Ca2+ store content. Further, the diminished Ca2+ signals in FXS and TS cells cannot be substantially attributed to diminished expression of IP3R proteins because IP3R expression showed little correlation with Ca2+ signaling depression (FIG. 3D).

To then discriminate whether the observed deficits in ATP-induced signals in FXS and TSC cells arose through defects in GPCR-mediated generation of IP3, or at the level of IP3-mediated Ca2+ liberation, the GPCR pathway was circumvented by loading cells with membrane permeant, biologically inert caged IP3 (ci-IP3). Concordant with defects in ATP-induced Ca2+ signals, global cytosolic Ca2+ responses evoked by photo-released i-IP3 in FXS cells were depressed and displayed slower kinetics. Corresponding measurements from TSC cells revealed even greater deficits in Ca2+ signal amplitudes.

Single-cell assays. Cells were loaded for imaging using membrane-permeant esters of Fluo-8 and c-IP3. Cells were incubated at room temperature in HEPES-buffered saline (in mM: NaCl 135, KCl 5, MgCl2 1.2, CaCl2) 2.5, HEPES 5, and glucose 10) containing 1 μM ci-IP3/PM for 45 mins, after which 4 μM Fluo-8 AM was added to the loading solution for a further 45 minutes before washing three times with saline solution. [Ca2+]i changes were imaged using a super-resolution N-STORM Nikon Eclipse microscope system with a 40× (NA=1.30) objective. Fluo-8 fluorescence was excited by 488 nm laser, and emitted fluorescence ($\lambda > 510$ nm) was imaged at 30 frames sec-1 using an electron-multiplied CCD Camera iXon DU897 (Andor).

Photolysis of c-IP3 was evoked by a millisecond standardized single flash of UV (ultraviolet) light (350 to 400 nm) from an arc lamp focused to uniformly illuminate a region slightly larger than the imaging frame to uncage biologically active IP3 from c-IP3, a metabolically stable and biologically inert isopropylidene analog of IP3. The amount of IP3 released is standardized by selecting a flash duration, but is ultimately a function of several factors, including length of the flash, power of the Arc lamp, and neutral density filters inserted on the light path. Image data were acquired as stack .nd2 files using Nikon Elements for offline analysis using Nikon Elements. Calcium-evoked fluorescence signals from the whole cell are expressed as a ratio ($\Delta F/F0$) of changes in fluorescence ($\Delta F$) relative to the mean resting fluorescence at the same region before stimulation (F0). Bars represent standard error mean.

Figure 5A:
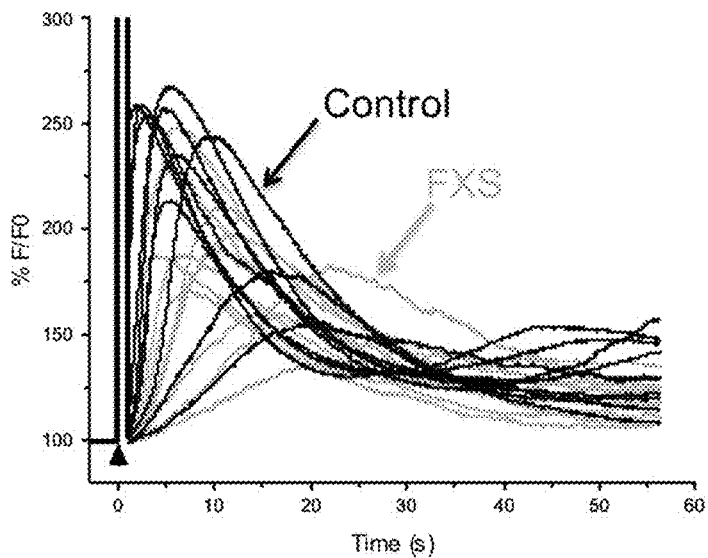
FIG. 5A shows a plot of calcium indicator Fluo-8 AM fluorescent traces of Ca$^{2+}$ release in individual control and FXS human skin fibroblast cells following photolysis of caged inositol triphosphate.
Figure 5B:
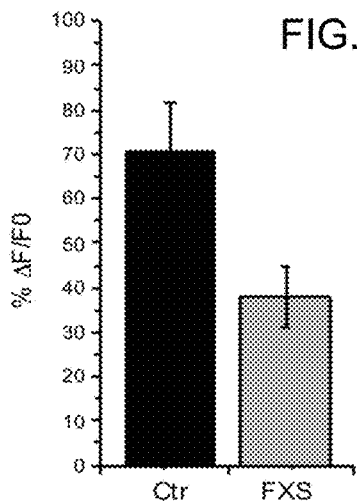
FIG. 5B shows a plot of mean peak Ca$^{2+}$ release exhibited by control and FXS skin fibroblast cells following photolysis of caged inositol triphosphate. All FxS lines are significantly different (p<0.05) from controls in the percent of cells responding with any calcium wave, the slope of the wave, the latency of the calcium wave and the peak height of the wave.
Figure 5C:
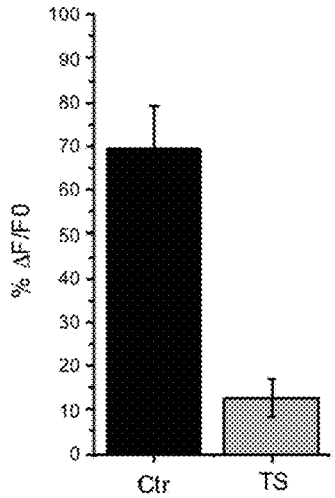
FIG. 5C shows a plot of mean peak Ca$^{2+}$ release exhibited by control and TS human skin fibroblast cells following photolysis of caged inositol triphosphate. All TS lines are significantly different (p<0.05) from controls in the percent of cells responding with any calcium wave, the slope of the wave, the latency of the calcium wave and the peak height of the wave. Fluorescence signals are expressed as a ratio (ΔF/F0) of changes in fluorescence (ΔF) relative to the mean resting fluorescence of the same well before stimulation (F0).

UV flash photolysis of cells loaded with biologically inert c-IP3 to photorelease active IP3 bypasses the GPCR signaling pathway and produces IP3 mediated IP3R activation. By controlling UV flash length and intensity, equivalent quantities of active IP3 were delivered to both control and FXS and TS cells, stimulating Ca2+ release. Consistent with the observations of defects in ATP-induced Ca2+ signaling in FX and TS cells, defects in global Ca2+ signaling were also observed in FXS and TS cells following UV flash photolysis of c-IP3 (FIGS. 5A-5C).

Figure 4A:
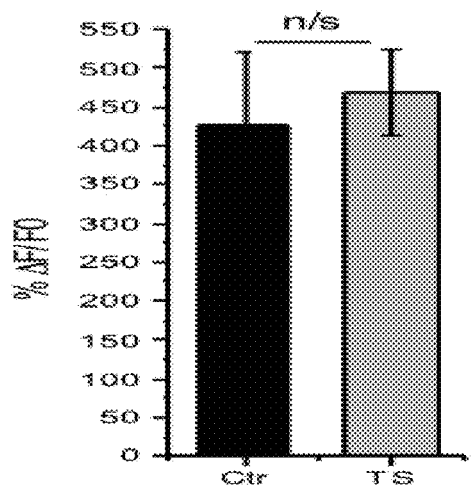
FIG. 4A shows a plot of mean peak Ca$^{2+}$ release exhibited by control and TS human skin fibroblast cells loaded with calcium indicator Fluo-8 AM in response to ionomycin, a potent and specific calcium ionophore. Three TS and three corresponding control cell lines were combined and averaged, and demonstrate no difference between cells in maximal calcium signal (the calcium pool size). Fluorescence signals are expressed as a ratio (ΔF/F0) of changes in fluorescence (ΔF) relative to the mean resting fluorescence of the same well before stimulation (F0).
Figure 4B:
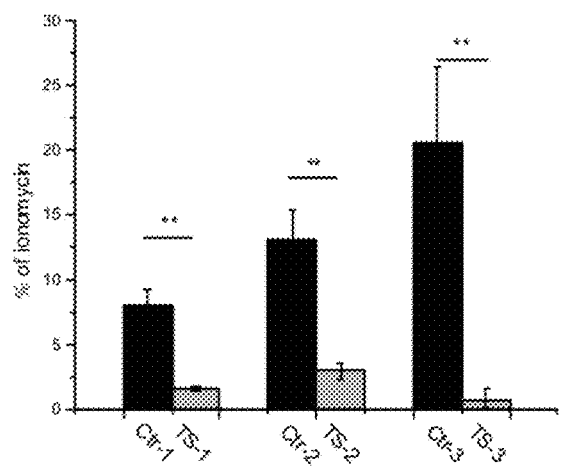
FIG. 4B shows a plot of mean peak Ca$^{2+}$ release exhibited by individual control and TS skin fibroblast cells induced with ATP normalized to corresponding maximal response to ionomycin. Similar to the effects observed in FIG. 3B for the FSX cell lines, all TS lines are significantly different (p<0.05) from controls.
Figure 4C:
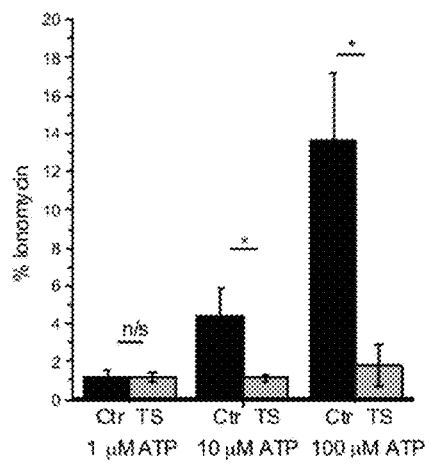
FIG. 4C shows a mean response of TS and control cell lines to various concentrations of ATP.

The results of these experiments indicate that the peak ATP-induced release of Ca2+ in 0 Ca2+ solution is significantly ($p<0.05$) depressed in the FXS and TS patient fibroblast lines, as compared to matched control cell lines (FIGS. 3B and 4B). This depression is not simply due to deficits in ER Ca2+ stores as application of the Ca2+ ionophore ionomycin in Ca2+-free media, which completely liberates all intracellular Ca2+ stores, demonstrated similar total Ca2+ content in FXS and control fibroblast cells (FIG. 3A) as well as TS and control fibroblast cells (FIG. 4A).

These results suggest that the defect in Ca2+ signaling in these three independent ASD models is not due to altered signaling to the IP3R via the GPCR or IP3 pathway, but instead implicates altered IP3R function.

Example 2 IP3-Signaling is Affected at the Level of Local Events

Figure 6A:
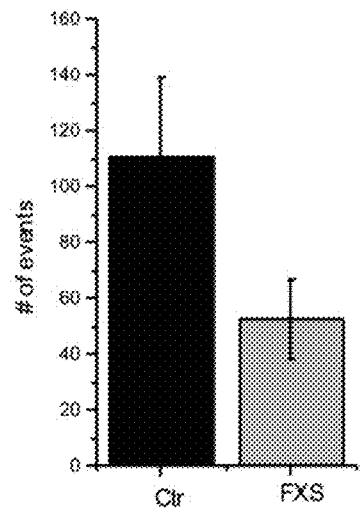
FIG. 6A shows a plot of the number of local Ca$^{2+}$ events in control and FXS human skin fibroblast cells loaded with EGTA and Fluo-8 AM and following photolysis of caged inositol triphosphate.
Figure 6B:
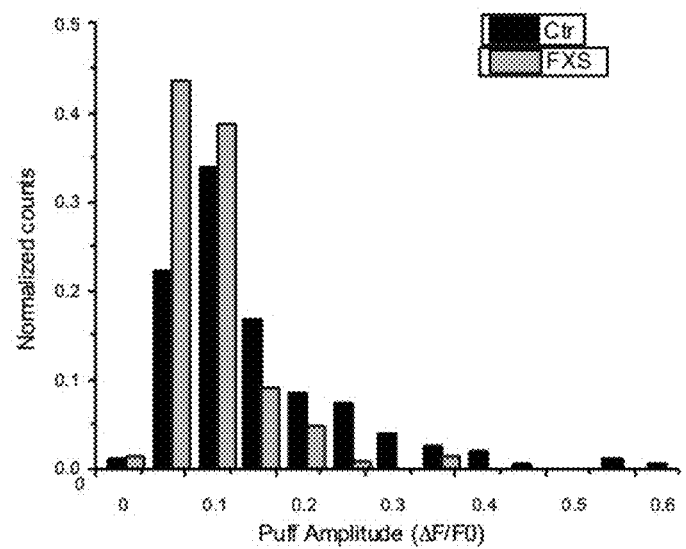
FIG. 6B shows a distribution of local Ca$^{2+}$ events of various amplitude in control and FXS cells following photolysis of caged inositol triphosphate. It demonstrates FXS cells to have a preponderance of small local events and a deficit of large events compared to control.

Without being bound by any particular theory, experimental data support a model in which IP3-mediated Ca2+ signaling exists as a hierarchy of Ca2+ events of differing magnitudes. In this model, a coordinated recruitment of clusters of IP3Rs located on the ER is responsible for generating global Ca2+ waves. It is possible that deficits in global Ca2+ waves observed in FXS and TS human skin fibroblasts result from alterations in local Ca2+ signals. Control and FXS skin fibroblasts were then loaded with the Ca2+ buffer EGTA to restrict the diffusion of Ca2+ between puff sites and prevent CICR between clusters of IP3Rs. In this way global Ca2+ waves can be devolved into multiple discrete puff sites whereupon the kinetics of Ca2+ release from IP3Rs can be observed. Cells were stimulated by photo-release of c-IP3 as described above, and individual puffs were resolved, and the results graphed in FIG. 6. FIG. 6A shows that number of local events is lower in FXS compare to control cells. Puff amplitude distribution in FXS cells is shifted toward smaller events, whereas control cells have more events with larger amplitude (FIG. 6B), corresponding to a bigger local Ca2+ release. In a physiological setting without the EGTA present, larger elementary Ca2+ events should be more successful in activating neighboring clusters, leading to further IP3R activation. The net result should be a higher probability of successful production of calcium waves that arise with a shorter latency, steeper slope and larger maximum, as is observed in FIGS. 3-5. These results suggest that IP3-mediated Ca2+ signaling in FXS cells is altered at the level of both local and global IP3R signals.

Figure 2:
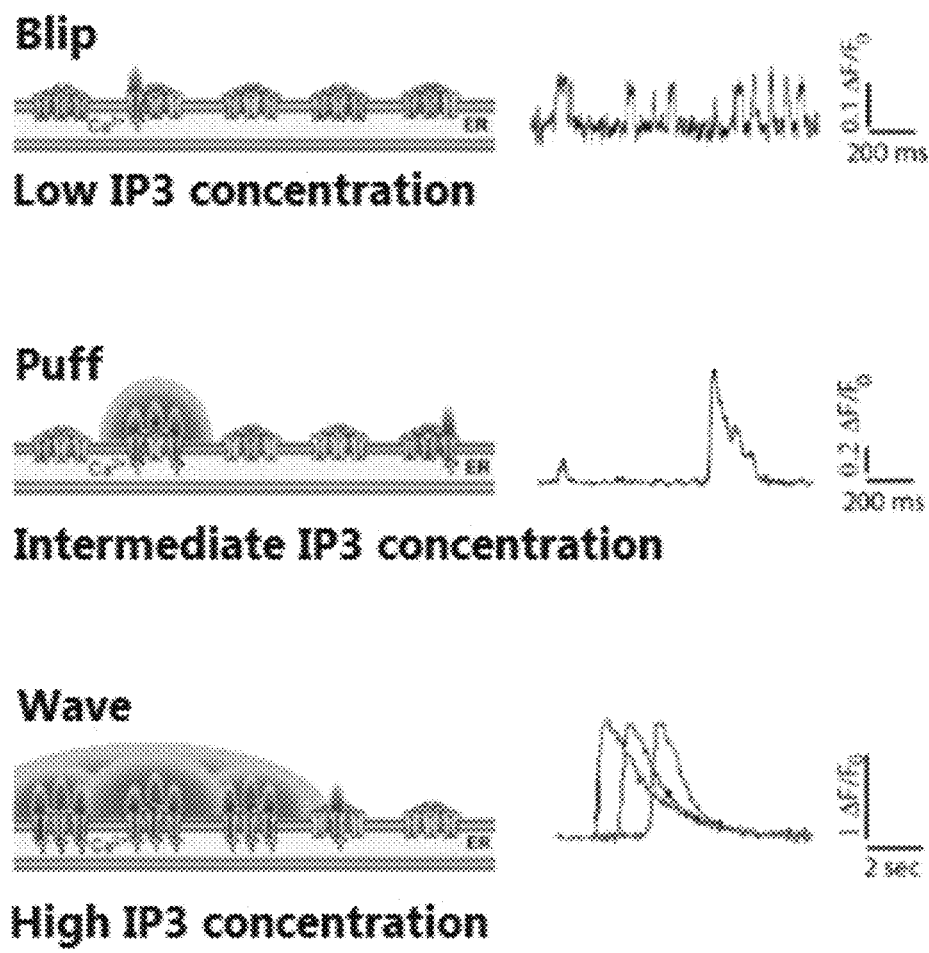
FIG. 2 shows a cartoon illustration of a proposed spatial organization of IP$_3$R in endoplasmic reticulum (ER) membrane.

IP3-mediated cellular Ca2+ signaling is organized as a hierarchy, wherein global, cell-wide signals arise by recruitment of local, 'elementary' events involving individual IP3R or small numbers of IP3Rs (FIG. 2). These elementary events were then imaged to elucidate how deficits in the global Ca2+ signals in FXS and TSC cells may arise at the level of local IP3R clusters and individual channels. Ca2+ release evoked by spatially uniform photolysis of ci-IP3 across the imaging field was apparent as localized fluorescent transients of varying amplitudes, arising at numerous discrete sites widely distributed across the cell soma (FIGS. 8A-8B). To quantify differences in elementary Ca2+ events between the cell lines, a custom-written, automated algorithm was utilized to detect events and measure their durations, numbers and amplitudes. Local events were appreciably briefer in FXS and TSC cells (FIG. 8C), suggesting a shortening in mean open time of IP3R channels. A second key difference lay in the numbers of detected sites, which were strikingly different between control and ASD lines (FIG. 8D), although mean event amplitudes were similar (FIG. 8E).

Example 3 cAMP Partially Restores Ca2+ Signaling in FXS Human Fibroblasts

Several kinases modulate IP3R Ca2+ signaling, including protein kinase A (PKA). PKA is a cAMP-dependent kinase, and reduced levels of cAMP have been shown to exist in *drosophila* and mouse FXS models, as well as in peripheral blood of human FXS subjects. To determine whether altered PKA activity leads to decreased IP3 Ca2+ signaling in FXS skin fibroblasts, the inventors conducted assays with the cell membrane permeant cAMP analog, 8-bromo-cAMP.

Fibroblast skin cells were loaded for imaging using membrane-permeant esters of Fluo-8 AM and c-IP3 and imaged as described above. Global Ca2+ responses were obtained before and after 20 minute incubation with 25 uM 8-bromo-cAMP (Tocris, cat. #1140). Image data were acquired as stack .nd2 files using Nikon Elements for offline analysis using Nikon Elements. Fluorescence signals are expressed as a ratio (ΔF/F0) of changes in fluorescence (ΔF) relative to the mean resting fluorescence at the same region before stimulation (F0). Bars represent standard error mean.

Figure 7:
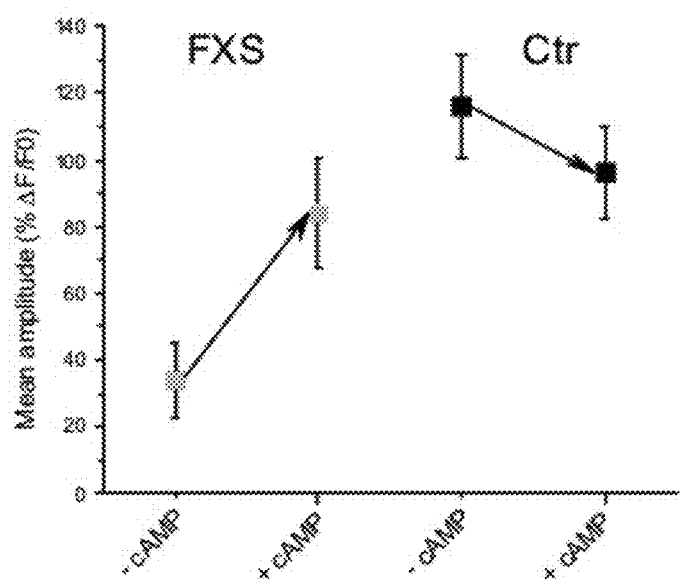
FIG. 7 is a plot of mean peak $Ca^{2+}$ release exhibited by FXS and matching control human skin fibroblast cell lines treated with 0 μM cyclic adenosine monophosphate (cAMP) or 25 μM cAMP following photolysis of caged inositol triphosphate. It demonstrates a normalization of the calcium signal by cAMP in FXS cells, comparable to control, with little effect on control cells.

Incubation of skin fibroblasts with 8-bromo-cAMP partially rescued the dampened global Ca2+ response to photo-release of IP3 observed in human FXS skin fibroblast cells (FIG. 7, left). Strikingly, cAMP had minimal effect on control cells, actually tending to lower the peak amplitude (FIG. 7, right).

Figure 9A:
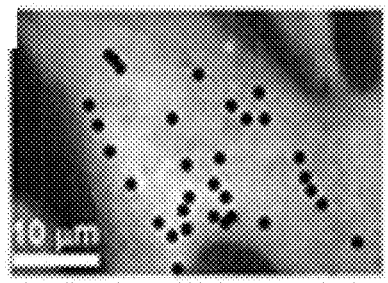
FIGS. 9A-9E show reduced constitutive Ca2+ signals in FXS and elevated autophagy markers in FXS, TSC, and ASD.
Figure 9B:
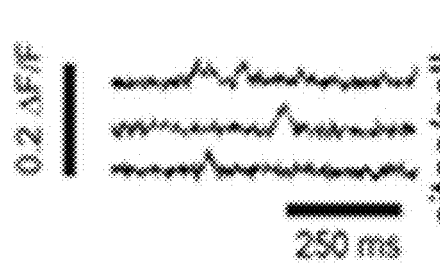
Figure 9C:
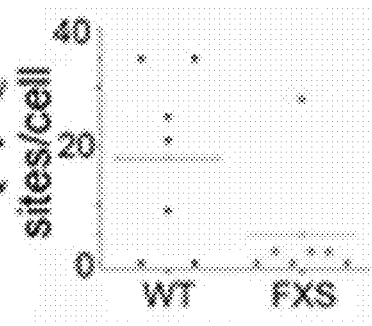
Figure 9D:
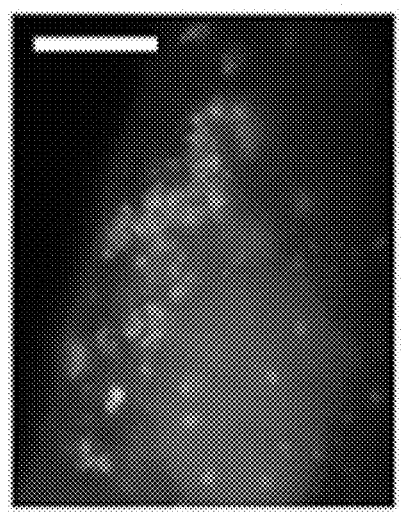
Figure 9E:
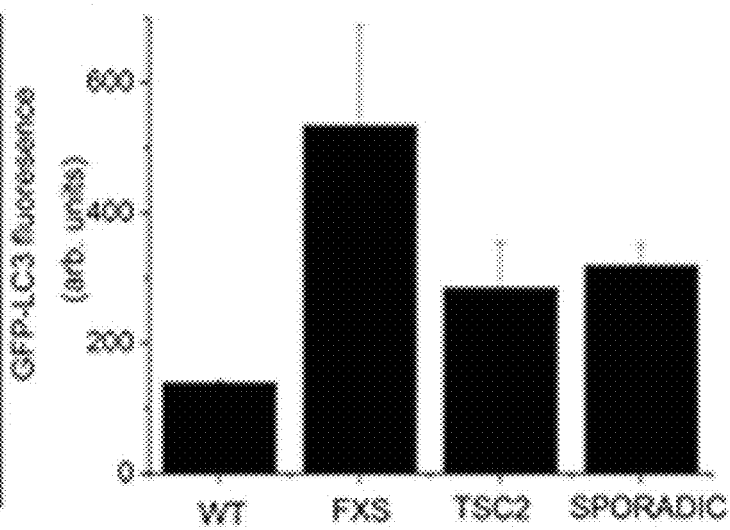

Example 4 Mitochondrial Energetics; a Putative Link Between Disrupted $Ca^{2+}$ and ASD Low-level constitutive IP3R-mediated transfer of Ca2+ from the ER to mitochondria maintains basal levels of oxidative phosphorylation and ATP production. In its absence, ATP levels fall, inducing AMPK-dependent, mTOR-independent autophagy. Because of the mitochondrial energy deficient endophenotypes of autism, this study investigated whether constitutive Ca2+ signaling is impaired in ASD fibroblasts, leading to autophagy. Fibroblasts from FXS subjects displayed fewer sites of local constitutive Ca2+ release than control cells (5±4 vs. 18±6 per cell), and while single channel amplitudes were similar, with channel open time reduced, total calcium flux was decreased in FXS. (FIGS. 8C and 9C) To then investigate whether autophagy is upregulated in ASD, GFP-LC3 (a marker for autophagosomes) was expressed in fibroblasts from WT, FXS, TSC2 and a sporadic ASD subject recently enrolled in CART. GFP-LC3 fluorescence was significantly elevated in all ASD cases versus control (FIGS. 9D-9E). Significant elevations of lysotracker red fluorescence marking acidic lysosomes that bind autophagosomes were observed.

Figure 10A:
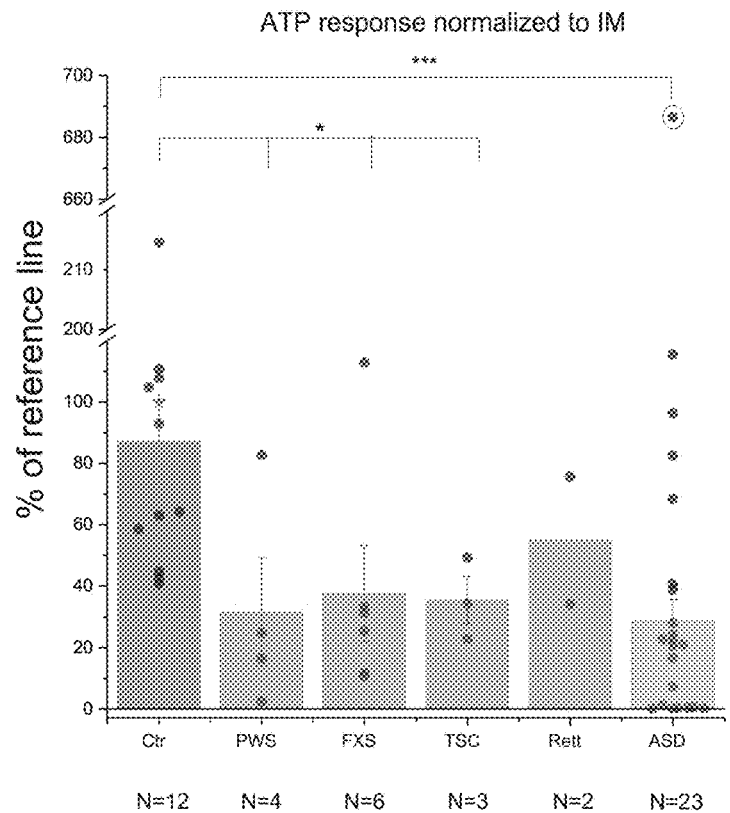
FIG. 10A shows the ATP response in fibroblasts from a highly heterogenous cohort of subjects sporadic ASD as well as from controls and those with syndromic ASD and as percent of a reference cell line. Average Ca2+ response in skin fibroblasts from unaffected neurotypical controls (Ctr), Prader-Willi syndrome (PWS), fragile X syndrome (FXS), tuberous sclerosis syndrome 1 and 2 (TSC), Rett syndrome (Rett) and from subjects with sporadic ASD (ASD). N below each cell line represents number of individuals tested. (GM03440) run on the same FLIPR plate. Bar graphs show mean+/−SEM for each group. Data points represent responses from an individual.
Figure 10B:
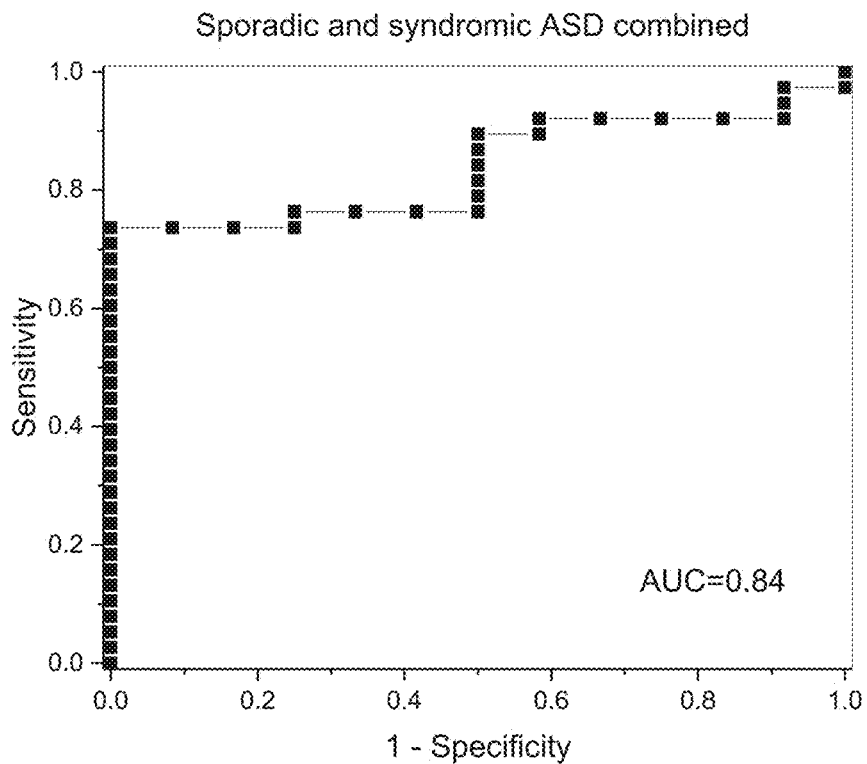
FIG. 10B shows an ROC Curve showing 73% sensitivity and 92% specificity of the high throughput assay in discriminating ASD samples from control samples.
Figure 11A:
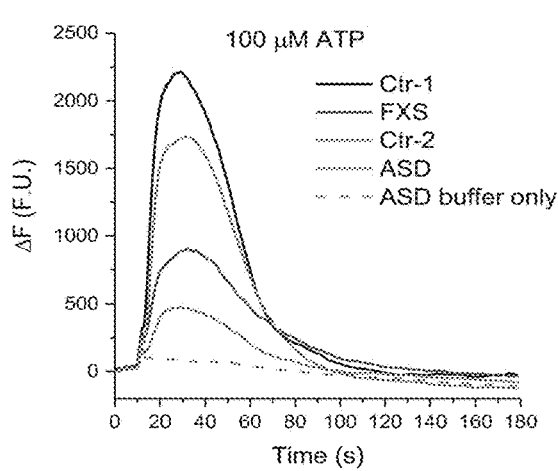
FIG. 11A shows traces of ATP-induced $Ca^{2+}$ events in zero $Ca^{2+}$ solution.
Figure 11B:
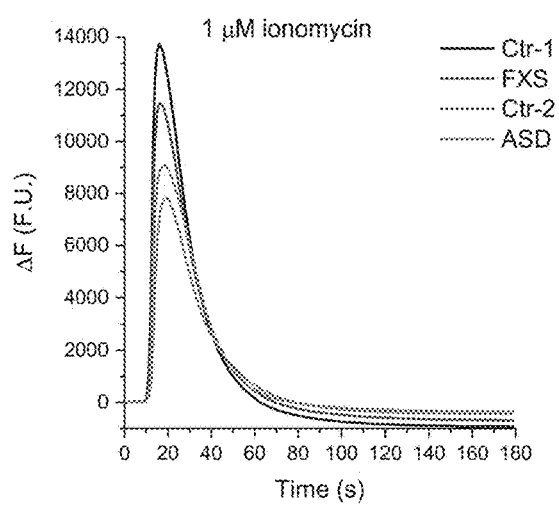
FIG. 11B shows traces of ionomycin-induced (IM) $Ca^{2+}$ events in zero $Ca^{2+}$ solution.
Figure 11C:
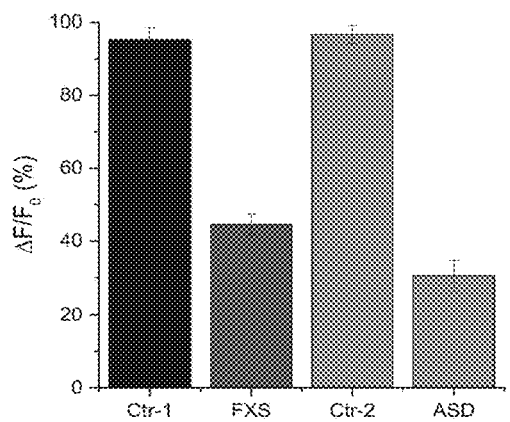
FIG. 11C shows percent change of $Ca^{2+}$ release relative to basal measurement in ATP induced $Ca^{2+}$ signaling.
Figure 11D:
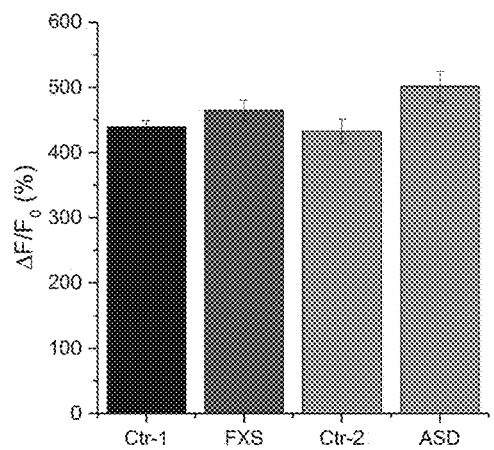
FIG. 11D shows maximum $Ca^{2+}$ release relative to basal signal in IM induced $Ca^{2+}$ signaling.
Figure 11E:
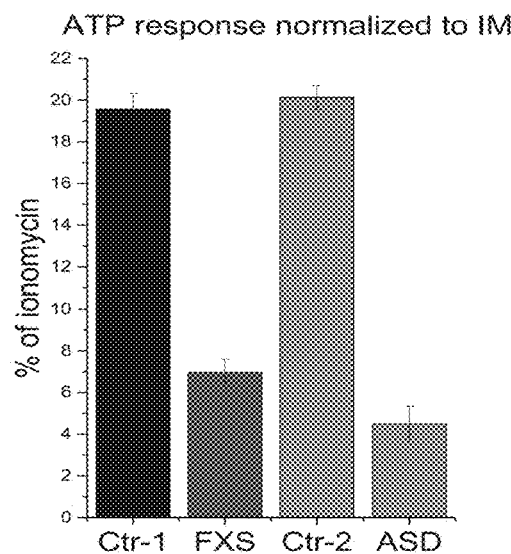
FIG. 11E shows normalized values of ATP responses to IM responses.

Example 5 Discriminating Between Syndromic or Sporadic ASD Samples and Controls Using Receiver Operator Characteristic (ROC) Curves Currently, ASD is diagnosed using clinical, behavioral assessments that may be subject to human error. Without wishing to limit the present invention to any theory or mechanism, the invention uses intracellular calcium signaling as an ASD biomarker that can be detected using in vitro high throughput assay measurements. An ROC curve evaluates parameters to separate affected from unaffected individuals for diagnostic purposes. The area under the curve (AUC) in FIG. 10B shows that the assay of the present invention is quite robust (84% accuracy) in discriminating between syndromic or sporadic ASD samples and controls. Using the reference shown in FIG. 10A, 73% sensitivity and 92% specificity of the high throughput assay is observed in discriminating ASD samples from control samples. FIG. 10A shows that $IP_3$-mediated $Ca^{2+}$ response is significantly depressed across monogenic and sporadic forms of ASD.

Example 6 High-Throughput FLIPR Screen to Monitor $IP_3$-Mediated $Ca^{2+}$ Signaling Changes in Response to Purinergic Activation A high-throughput screen using FLIPR was developed to monitor $IP_3$-mediated $Ca^{2+}$ signaling in the monogenic ASD and typical, sporadic ASD samples. FIGS. 11A-11E show representative $IP_3$-mediated $Ca^{2+}$ signaling changes in response to purinergic activation and demonstrate that Ca2+ signals in response to ATP activation are lower in ASD and FSX samples.

IP3 signaling in the FLIPR assay is activated by bath application of an agonist (e.g., ATP) to activate metabotropic purinergic receptors. This introduces complications and potential variability in the pathway leading to IP3 production. To circumvent that, the present invention features a method for delivering IP3 directly to the ER of permeabilized fibroblasts. This will be based on established protocols utilizing a low-affinity fluorescent Ca2+ indicator (furaptra) trapped in the lumen of the ER and agents (e.g. saponin, streptolysin-O) to selectively permeabilize the cholesterol-rich plasma membrane, while sparing the cholesterol-poor ER. Moreover, this method will enable one to control and investigate variability that may arise from intracellular factors (such as ATP concentration, cytosolic Ca2+ buffers, phosphatases and kinases) known to modulate IP3R functioning.

Example 7 Human-Induced Pluripotent Stem Cells

Human induced pluripotent stem cells (hiPSCs) were generated from the fibroblasts using the Thermo-Fisher Sendai virus protocol. For the differentiation, hiPSCs form EBs in suspension culture for the first 7 days and then are plated and develop into colonies containing rosette, neuroepithelial cells. At day 16, neural progenitors can be observed in the edge and the rosette-containing colonies are detached and grown in suspension to form neuroepithelial sphere.

Figure 12A:
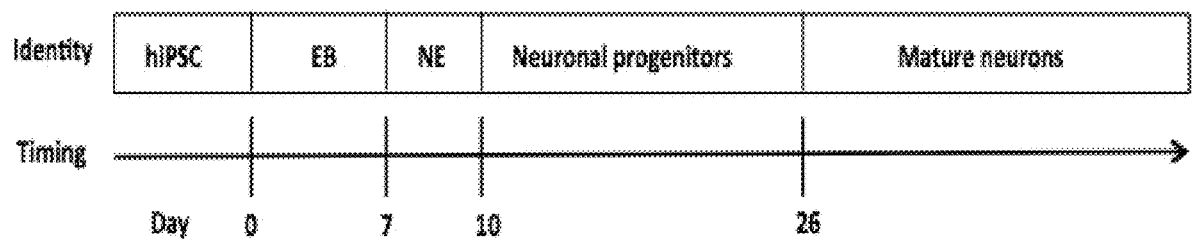
FIG. 12A shows that differentiation of human iPSC to GABA interneurons involves 4 stages, including embryonic body (EB) formation, induction of neuroepithelial cells (NE), patterning of MGE progenitors and differentiating to GABA neurons.
Figure 12B:
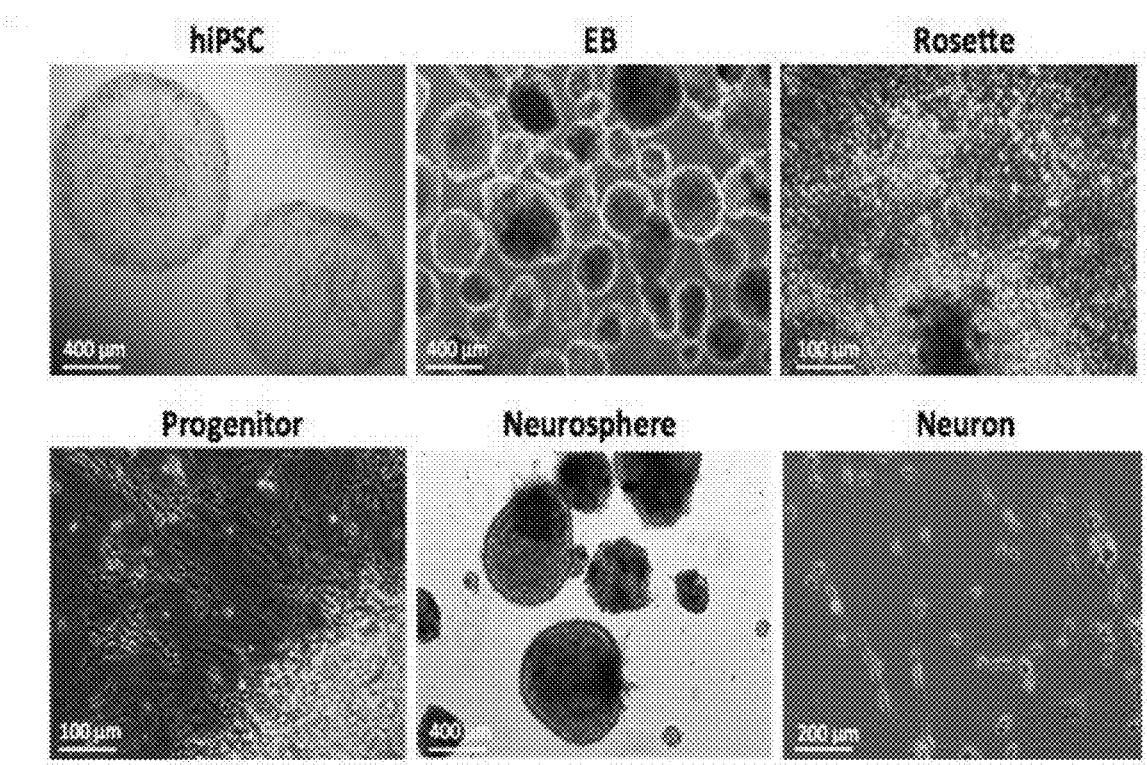
FIG. 12B shows that under a defined system, hiPSCs were differentiated into neurons.
Figure 13A:
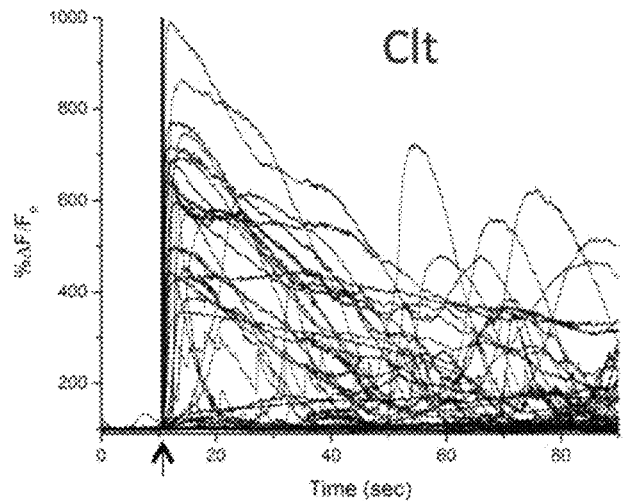
FIGS. 13A-13C show $IP_3$-mediated $Ca^{2+}$ signaling is decreased in neuronal progenitors from an FXS patient, similar to fibroblasts.
Figure 13B:
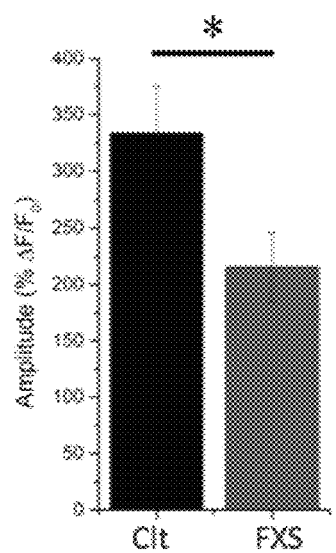
Figure 13B:
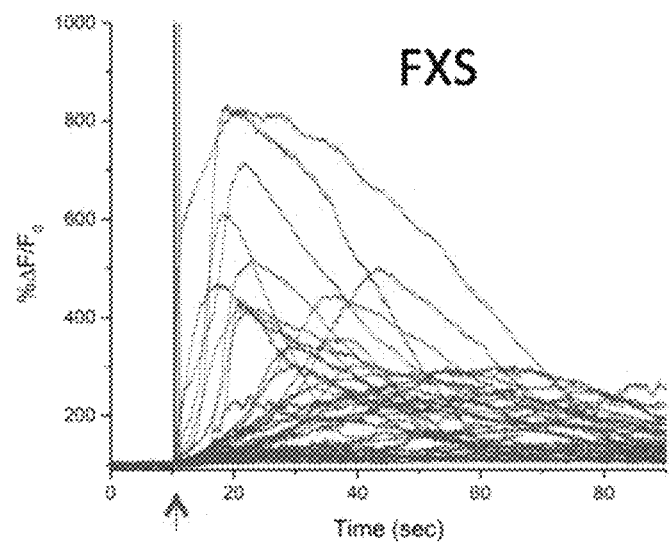
Figure 13C:
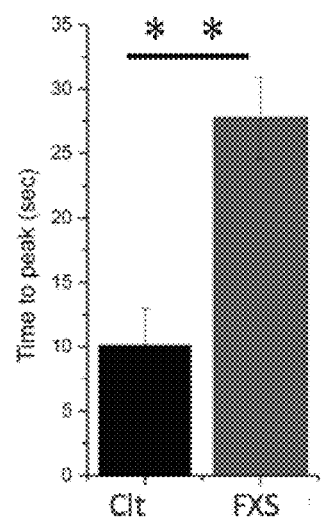

Differentiation of human iPSC to GABA interneurons involves 4 stages, including embryonic body (EB) formation, induction of neuroepithelial cells (NE), patterning of MGE progenitors and differentiating to GABA neurons (FIG. 12A). Under a defined system, hiPSCs were differentiated into neurons (FIG. 12B). FIG. 13 shows $IP_3$-mediated $Ca^{2+}$ signaling is decreased in neuronal progenitors from an FXS patient, similar to fibroblasts.

Figure 14A:
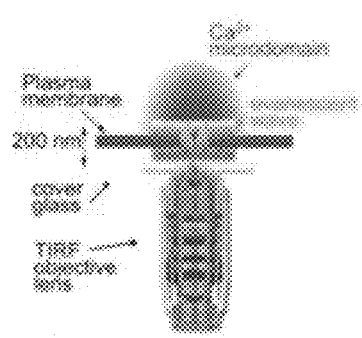
FIGS. 14A-14E show optical single channel recording using optical patch clamp technique.
Figure 14B:
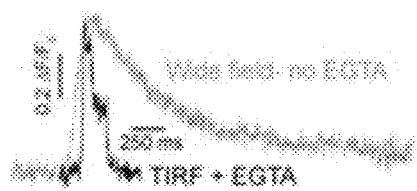
Figure 14C:
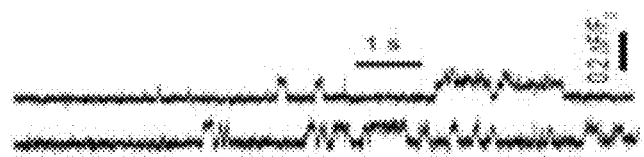
Figure 14D:
Figure 14E:
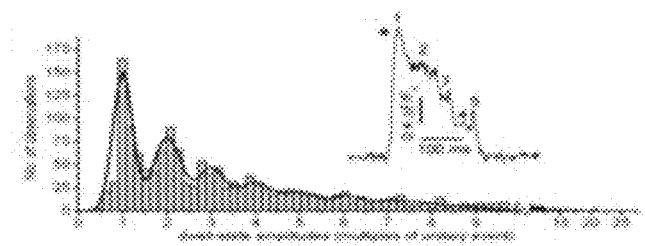

Example 8 Technical Innovation: $Ca^{2+}$ Fluorescence Signals from Individual $IP_3Rs$; the Optical Patch Clamp The optical patch-clamp technique allows the imaging of $Ca^{2+}$ flux through single ion channels within intact cells with single channel resolution. Total internal reflection microscopy (TIRFM) (FIG. 14A) together with a slow $Ca^{2+}$ buffer (FIG. 14B) is used to restrict excitation of a cytosolic fluorescent $Ca^{2+}$ indicator to within ~100 nm of the plasma membrane, thereby monitoring the local microdomain of elevated cytosolic $[Ca^{2+}]$ around the pore of $Ca^{2+}$-permeable membrane channels. The resulting localized single-channel $Ca^{2+}$ fluorescence transients (SCCaFTs) turn on and off rapidly, tracking channel openings and closings with a time resolution of a few milliseconds (FIG. 14C). Using this technique, the $Ca^{2+}$ puffs arising from clusters of $IP_3Rs$ (FIG. 14D) can be dissected into the constituent openings and closings of individual receptor/channels (FIG. 14E).

As disclosed herein, reduced IP3-mediated Ca2+ signaling was shown in ASD in the context of fragile X (FXS) and tuberous sclerosis syndromes (TS). The inventors found that human fibroblasts from three genetically distinct monogenic models of ASD-fragile X and tuberous sclerosis TSC1 and TSC2—uniformly display depressed Ca2+ release through IP3 receptors. They observed defects in whole-cell Ca2+ signals evoked by G-protein coupled cell surface receptors and by photo-released IP3, and at the level of local elementary Ca2+ events, suggesting fundamental defects in IP3R channel activity in ASD. Given its ubiquitous functions in the body, malfunctioning of IP3-mediated signaling can account for the heterogeneity of non-neuronal symptoms seen in ASD, such as gastrointestinal tract problems and immunological complications.

In summary, these results provide compelling evidence that IP3-mediated Ca2+ signaling is a common phenotype and a shared functional defect in three distinct monogenic models of ASD. The implications of this work are: GPCR-triggered intracellular Ca2+ release is decreased in three distinct monogenic modes of ASD; These pathological alterations are downstream of IP3 generation, as similar results are obtained using UV flash photolysis of membrane permeant caged IP3-AM; TIRFM imaging determined that a striking difference between control and ASD lines arose in the numbers of detected sites and the durations of the local events; IP3-mediated Ca2+ signaling is a common biomarker and a possible therapeutic target for ASD; and alterations in Ca2+ homeostasis can be a common pathogenic mechanism in ASD and explain the heterogeneity of its symptoms.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

What is claimed is:

1. A method, comprising:
   (a) obtaining a biological sample from a human;
   (b) independently culturing the cells from (a);
   (c) adding an agonist of $IP_3R$ $Ca^{2+}$ signaling to the cultured cells from (b); and
   (d) measure the level of inositol triphosphate receptor ($IP_3R$) calcium ($Ca^{2+}$) signaling activity in the cultured cells from (b) induced by an agonist of $IP_3R$ $Ca^{2+}$ signaling using a $Ca^{2+}$ fluorescent probe and measuring the amount of fluorescence emitted by the probe;
   wherein the agonist of $IP_3R$ $Ca^{2+}$ signaling comprising of adenosine triphosphate and a caged inositol triphosphate.

2. The method of claim 1, wherein the biological samples comprise skin, foreskins, amniotic fluid, blood, and/or, cheek-swabbed epithelial cells.

3. The method of claim 1, wherein the $Ca^{2+}$ fluorescent probe is an intracellular-loaded fluorescent calcium indicator dye and comprises at least one member selected from the group consisting of a Fluo-8 AM, a Fluo-3, a Fluo-4, a Rhod-2; a Cal 520; a Calcium Green, a Calcium Orange; an Oregon Green BAPTA; a Fura Red; and a GCaMP.

4. The method of claim 1, wherein the emitted fluorescence is measured using a fluorometer, fluorescent imaging plate reader (FLIPR).

* * * * *